United States Patent [19]
Dunn

[11] Patent Number: 5,736,591
[45] Date of Patent: Apr. 7, 1998

[54] LATEX WITH RESISTANCE TO BACTERIAL GROWTH

[75] Inventor: Edwin Reed Dunn, Rocky Face, Ga.

[73] Assignee: The Goodyear Tire & Rubber Co., Akron, Ohio

[21] Appl. No.: 609,405

[22] Filed: Mar. 1, 1996

[51] Int. Cl.$^6$ .......................... C08K 3/10; A01N 59/16; A01N 59/20

[52] U.S. Cl. .......................... 523/122; 524/403; 524/413; 424/618; 424/630; 424/649

[58] Field of Search .......................... 523/122; 524/403, 524/413; 424/618, 630, 649

[56] References Cited

U.S. PATENT DOCUMENTS

| | | | |
|---|---|---|---|
| 4,291,125 | 9/1981 | Greatbatch | 435/240 |
| 4,442,095 | 4/1984 | Johnston | 424/248.5 |
| 4,481,202 | 11/1984 | Johnston | 424/250 |
| 4,507,299 | 3/1985 | Johnston | 514/255 |
| 4,512,991 | 4/1985 | Johnston | 514/252 |

Primary Examiner—Kriellion S. Morgan
Attorney, Agent, or Firm—Alvin T. Rockhill

[57] ABSTRACT

The growth of bacteria in latex is an age old problem. To control the growth of bacteria in latex, chemical bactericides are often added to latex. This invention discloses a technique for providing latex with resistance to bacterial growth. It is based upon the discovery that ions of a metal from Group Ib of the Periodic Chart, such as copper, silver, or gold, will provide latex with resistance to bacterial growth. The subject invention more specifically discloses a latex which is comprised of (1) a polymer, (2) water, (3) an emulsifier and (4) ions of a metal from Group Ib of the Periodic Chart. In most cases, the metal ions will be present in an amount which is within the range of about 1 ppm to about 50 ppm. As a general rule, silver ions are preferred. By utilizing a combination of standard organic chemical bactericides and Group Ib metal ions, the level of chemical bactericides and metal ions needed to satisfactorily control bacteria growth can be significantly reduced. Such a combination of chemical bactericides and Group Ib metal ions accordingly offers excellent cost advantages and provides treated latex with a high degree of protection against bacterial growth. The present invention further reveals a latex which is comprised of (1) a polymer, (2) water, (3) an emulsifier, (4) ions of a metal from Group Ib of the Periodic Chart and (5) an organic chemical bactericide.

20 Claims, No Drawings

LATEX WITH RESISTANCE TO BACTERIAL GROWTH

BACKGROUND OF THE INVENTION

Latex is utilized in a wide variety of applications. For instance, it is used in making water-based paints, which are also known as latex paints (see U.S. Pat. No. 4,968,741), in manufacturing carpet backing, in asphalt modification (see U.S. Pat. No. 5,002,987), in manufacturing latex rubber products, such as rubber gloves, and in a wide variety of other applications.

After being manufactured, the latex is usually held in inventory, shipped and stored before being used. During this period of time, certain types of bacteria can grow in the latex. Such bacterial growth can destroy the properties of the latex and can cause undesirable odors. In some cases, bacterial growth can completely destroy the latex rendering it unsuitable for use in manufacturing latex products. In other cases, bacteria can later grow in latex products, such as latex paint, destroying the desirable characteristics of the product and causing undesirable characteristics, such as discoloration and odors. In any case, it is highly undesirable for bacteria to be allowed to freely grow in latex and latex products.

Bactericides are often added to latex to limit the growth of bacteria. U.S. Pat. No. 4,442,095, U.S. Pat. No. 4,442,096, U.S. Pat. No. 4,442,097, U.S. Pat. No. 4,481,202, U.S. Pat. No. 4,507,299, U.S. Pat. No. 4,512,991 and U.S. Pat. No. 4,517,186 disclose the use of chemical bactericides to control the growth of bacteria in latex. For instance, U.S. Pat. No. 4,481,202 discloses a method of inhibiting the growth of bacteria and fungi in latex paints and latex emulsions and adhesives which comprises incorporating into the latex paints, emulsions and adhesives so as to contact said bacteria and fungi, at least a bactericidally and fungicidally effective amount of certain chemical bactericides, such as n-octyl (2-amino-5-chloro-6-(n-octylthio)pyrazinyl)formate, n-octyl (2-amino-5-chloro-6-(n-methylthio)pyrazinyl) formate, and n-octyl (2-amino-5-chloro-6-((1-methylethyl)thio)pyrazinyl) formate.

Chemical bactericides which can be used to control the growth of bacteria in latex are generally expensive. Even when added to latex in relatively small amounts, the use of such chemical bactericides can increase the cost of manufacturing latex significantly and, in some cases, do not provide the treated latex with a satisfactory degree of protection against bacterial growth. Also, in some cases, chemical bactericides cause discoloration of the treated latex. The use of many chemical bactericides is undesirable because they generate formaldehyde.

U.S. Pat. No. 5,478,467 discloses a water purification device for attachment to a hose or other water supply such that water flowing through the device comes in intimate contact with a treatment media including free available silver ions to provide a germicide and antibacterial treatment of the water flowing therethrough. U.S. Pat. No. 5,470,585 discloses the use of silver ions for bacteria control on medicinal substances, such as pads, towels and tampons. U.S. Pat. No. 5,464,559 discloses a composition for treating water with resin bound ionic silver.

SUMMARY OF THE INVENTION

This invention is based upon the discovery that ions of metals from Group Ib of the Periodic Chart, such as copper, silver and gold, can inhibit the growth of bacteria in latex. By adding ions of Group Ib metals to latex, the growth of bacteria therein is greatly inhibited. In other words, Group Ib metal ions can be added to latex as a bacterial control agent.

The subject invention more specifically discloses a latex which is comprised of (1) a polymer, (2) water, (3) an emulsifier and (4) ions of a metal from Group Ib of the Periodic Chart.

The present invention further discloses a method of inhibiting the growth of bacteria in latex which comprises incorporating into the latex so as to contact said bacteria, at least a bactericidally effective amount of ions of a metal from Group Ib of the Periodic Chart.

The present invention is also based upon the unexpected discovery that Group Ib metal ions act synergistically with conventional chemical bactericides to kill and inhibit the growth of bacteria in latex. By utilizing a combination of standard organic chemical bactericides and Group Ib metal ions, the level of chemical bactericides and metal ions needed to satisfactorily control bacteria growth can be significantly reduced. Such a combination of chemical bactericides and Group Ib metal ions accordingly offers excellent cost advantages and provides treated latex with a high degree of protection against bacterial growth.

The present invention further reveals a latex which is comprised of (1) a polymer, (2) water, (3) an emulsifier, (4) ions of a metal from Group Ib of the Periodic Chart and (5) an organic chemical bactericide.

The present invention further discloses a method of inhibiting the growth of bacteria in latex which comprises incorporating into the latex so as to contact said bacteria, at least a bactericidally effective amount of ions of a metal from Group Ib of the Periodic Chart and an organic chemical bactericide.

DETAILED DESCRIPTION OF THE INVENTION

The technique of this invention can be employed to provide virtually any type of latex with a high degree of protection against bacterial growth at a relatively low cost. Such latices are comprised of (1) water, (2) at least one polymer and (3) an emulsifier (soap). The polymer can be any polymeric material which is capable of being in latex form. The polymer will generally be a homopolymer or copolymer of conjugated diolefin monomers, acrylic monomers, vinyl acetate monomers, vinyl pyridine, vinylidene monoaromatic monomers, vinyl aromatic monomers or α-olefin monomers. The latex can, of course, be a latex of a rubbery polymer. For instance, the latex can be a styrene-butadiene rubber latex, a carboxylated styrene-butadiene rubber latex, a polybutadiene rubber latex, a nitrile rubber latex or a carboxylated nitrile rubber latex.

The latices which can be treated by the process of this invention can contain a wide variety of types of emulsifiers or surfactants. For instance, synthetic surfactants can be employed. In many cases, salts of alkyl sulfates, alkyl sulfonates and alkyl phosphates will be utilized as the emulsifier. The alkyl groups in these compounds generally contain from 1 to 30 carbon atoms. Normally the alkyl groups in these surfactants will contain from 8 to 20 carbon atoms. The surfactant utilized will normally be a sodium, potassium, magnesium or ammonium salt. Sodium lauryl sulfate, ammonium lauryl sulfate, sodium dodecyl benzene sulfonate and sodium dodecyl sulfate are some representative examples of widely used emulsifiers.

Generally from about 0.005 phm (parts per 100 parts of monomer) to about 0.5 phm of emulsifier is utilized in preparing latices. In most cases, it is preferred for latex to contain from about 0.01 phm to 0.1 phm of emulsifier. It is normally more preferred for latex to contain from about 0.04 phm to about 0.08 phm of emulsifier. The precise amount of emulsifier required in order to attain optimal results will, of course, vary from one latex to another and with the specific emulsifier which is chosen. However, persons skilled in the art will be able to easily ascertain the specific amount of emulsifier required in order to attain optimal results.

Latices with extremely low solids contents to latices with extremely high solids contents can be treated by utilizing the techniques of this invention. For instance, the treated latex could have a solids content which is as low as about 1 percent to as high as about 70 percent. The latex will typically have a solids content which is within the range of about 30 percent to about 60 percent. The latex will more typically have a solids content which is within the range of about 45 percent to about 55 percent.

This method of this invention is carried out by simply adding ions of a Group Ib metal to the latex. This will typically be done shortly after the latex is synthesized. However, the Group Ib metal ions can be added to the water utilized in making the latex before the latex is made. On the other hand, the Group Ib metal ions can be added to the latex at any time in the storage life of the latex.

The Group Ib metal ions will normally be copper ions or silver ions for economic reasons. It is also, of course, possible to utilize a combination of silver ions and copper ions. Silver ions are normally most preferred. The metal ions can be added to the latex in the form of soluble compounds or as solutions of soluble compounds. For instance, silver acetate, silver bromide, silver carbonate, silver chlorate, silver chloride, silver citrate, silver fluoride, silver iodate, silver lactate, silver nitrate, silver nitrite, silver perchlorate or silver sulfide can be added directly to the latex. In the alternative, aqueous solutions of these compounds can be made with the solution being added to the latex. An electrolytic process for adding Group Ib metal ions to the latex can also be utilized.

The treated latex will normally contain from about 1 ppm to about 50 ppm (parts per million) of the Group Ib metal ions. In cases where the latex is treated with silver ions, it will more typically contain from about 2 ppm to about 10 ppm of silver ions. In most cases, it is preferred for the treated latex to contain from about 3 ppm to about 5 ppm of silver ions. In cases where copper ions are used, higher concentrations will normally be required.

To attain the most cost-effective level of protection against bacterial growth, a combination of Group Ib metal ions and organic chemical bactericide will typically be added to the latex. For instance, from about 2 ppm to about 4 ppm of silver ions can be added to the latex with about 300 ppm to 1000 ppm of an organic chemical bactericide. In some cases, it may be desirable to add more than one organic chemical bactericide to the latex in conjunction with the Group Ib metal ions. Numerous organic chemical bactericides which can be used in conjunction with Groups Ib metal ions are commercially available. Some representative of suitable organic chemical bactericides include: 2-methyl-4, 5-trimethylene-4-isothiazolin-3-one which is sold by Zeneca as an aqueous solution under the tradename Promexal X50, 1,2-dibromo-2,4-dicyanobutane which is sold by Calgon Corporation under the tradename Tektamer 38LV, 2-bromo-2-nitro-1,3-propanediol which is sold by Nalco under the tradename Nalco 92RU093, methylene bis(thiocyanate) which is sold in a mineral oil and water emulsion by Nalco under the tradename Nalco 5793, 1,2-dibromo-2,4-dicyanobutane which is sold by Calgon Corporation under the tradename Biochek 430, and 2-bromo-2-nitro-1,3-propanediol which is sold by Nalco under the tradename Nalco VX5357 as mixture with 2-methyl-4-isothiazolin-3-one and 5-chloro-2-methyl-4-isothiazolin-3-one.

This invention is illustrated by the following examples which are merely for the purpose of illustration and are not to be regarded as limiting the scope of the invention or the manner in which it can be practiced. Unless specifically indicated otherwise, all parts and percentages are given by weight.

EXAMPLES 1-4

In this series of experiments, a carboxylated styrene-butadiene rubber latex which was treated with 4 ppm of silver ions was compared for bacterial protection with a control and two latices which were treated with standard organic chemical bactericides. In the procedure used, quart (0.9464 liter) samples containing the bactericides were prepared and aged 20 days in a 37° C. water bath. One hundred wet grams of the aged latices were inoculated with 1 cc of latex containing about 6,000,000 cfu/cc of mixed wild strain bacteria. The inoculated latices were tested for active bacteria after 4 and 24 hours of aging at 37° C. and were then reinoculated with the spoiled latex. The latices were tested again 24 hours after the second inoculation.

In this series of experiments, Example 1 was conducted as a control and did not contain any bactericide or Group Ib metal ions. The latices tested in Examples 2 and 3 contained the combination of commercially available bactericides shown in Table I. The latex tested in Example 4 contained 4 ppm of silver ions which was introduced as a 0.1 percent silver nitrate solution. The results of these tests are shown in Table I.

TABLE 1

| | Bactericide Evaluations | | |
|---|---|---|---|
| Bactericide | 4 hrs | 24 hrs | 48 hrs |
| 1 Tektamer 38LV[1] - 1000 ppm Nalco 92RU093[2] - 150 ppm | $2.8 \times 10^4$ cfu/cc | 0 cfu/cc | 0 cfu/cc |
| 2 Nalco 5793[3] - 600 ppm Nalco 92RU093[2] - 200 ppm | $9.9 \times 10^4$ cfu/cc | $3.2 \times 10^5$ cfu/cc | $4.2 \times 10^6$ cfu/cc |
| 3 Silver ions - 4 ppm | $1.0 \times 10^2$ cfu/cc | 0 cfu/cc | 0 cfu/cc |
| 4 None | $2.8 \times 10^6$ cfu/cc | $6.4 \times 10^6$ cfu/cc | $6.0 \times 10^6$ cfu/cc |

[1]Tektamer 38LV biocide is a multicomponent dispersion which contains 25 percent by weight 1,2-dibromo-2,4-dicyanobutane.
[2]Nalco 92RU093 bactericide is an aqueous brominated nitroalcohol which is comprised of 2-bromo-2-nitro-1,3-propanediol in dipropylene glycol monoethyl ether.
[3]Nalco 5793 preservative is methylene bis(thiocyanate) in a mineral oil and water emulsion.

This experiment shows that the latex which was treated with 4 ppm silver ions was protected as well as the latex which was treated with 1000 ppm of Tektamer 38LV bactericide and 159 ppm of Nalco 92RU093 bactericide. The latex which was treated with 600 ppm of Nalco 5793 bactericide and 200 ppm of Nalco 92RU093 exhibited severe bacterial growth. The latex which was untreated also showed severe bacterial growth.

EXAMPLES 5-9

In this series of experiments, quart (0.9464 liter) samples of fresh carboxylated styrene-butadiene rubber latex containing various bactericides were prepared for testing. In the procedure used, 100 gram samples of the latices were repeatedly inoculated with 1.0 cc of a blend of six contaminated latices. The inoculated latices were stored in a 37° C. water bath and bacteria counts of the inoculated samples were taken the next working day. The samples were again inoculated with 1.0 cc of the contaminated latex with bacteria counts again being taken the next working day after being stored in the water bath at a temperature of 37° C. This procedure was repeated until the bactericides being tested failed. The bactericides tested as well as the number of inoculations required to cause failure are reported in Table II. The number of days to failure is also reported in Table II.

TABLE II

| Ex. | Bactericide | Inoculations | Days |
|---|---|---|---|
| 5 | Biochek 430[1] - 1500 ppm | 13 | 21 |
| 6 | Nalco VX5357[2] - 1500 ppm | 24 | 35 |
| 7 | Promexal X50[3] - 1000 ppm | 16 | 25 |
| 8 | Biochex 430[1] - 750 ppm Silver ions - 4 ppm | 16 | 25 |
| 9 | Silver ions - 4 ppm | 7 | 12 |

[1]Biochek 430 microbiocide is a multicomponent liquid which contains about 24 weight percent 1,2-dibromo-2,4-dicyano-butane, less than 0.1 weight percent 5-chloro-2-methyl-4-isothiazoline-3-one, and less than 0.1 weight percent 2-methyl-4-isothiazoline-3-one.
[2]Nalco VX 5357 bactericide is an aqueous solution of brominated nitroalcohol and substituted isothiazolinone which contains about 9.23 weight percent 2-bromo-2-nitro-1,3-propanediol, about 0.08 weight percent 2-methyl-4-isothiazolin-3-one, 0.23 weight percent 5-chloro-2-methyl-4-isothiazolin-3-one.
[3]Promexal X50 biocide is an aqueous solution of 2-methyl-4,5-trimethylene-4-isothiazolin-3-one.

As can be seen from Example 9 in Table II, the latex which contained only 4 ppm of silver ions as a bactericide protected the latex until the seventh inoculation over a period of 12 days. Thus, the silver ions alone provided the latex with protection against bacterial growth. However, Example 8 shows that outstanding protection against bacterial growth is provided by utilizing a combination of silver ions and organic chemical bactericide. In fact, the degree of protection against bacterial growth exhibited in Example 8 is better than the protection against bacterial growth exhibited in Example 5 where twice as much of the Biochek 430 bactericide was utilized.

EXAMPLES 10–16

The procedure described in Examples 5–9 was repeated in this series of experiments except for the fact that latex samples which had been shelf aged for one month were used rather than fresh latex samples. The results of this testing are reported in Table III.

TABLE III

| Ex. | Bactericide | Inoculations | Days |
|---|---|---|---|
| 10 | Biochek 430 - 1500 ppm | 3 | 4 |
| 11 | Nalco VX5357 - 1500 ppm | 21 | 37 |
| 12 | Promexal X50 - 1000 ppm | 8 | 14 |
| 13 | Biochex 430 - 750 ppm Silver ions - 4 ppm | 14 | 26 |
| 14 | Silver ions - 4 ppm | 5 | 8 |
| 15 | Nalco VX5357 - 750 ppm Silver ions - 2 ppm | 21 | 37 |
| 16 | Promexal X50 - 500 ppm Silver ions - 4 ppm | 7 | 13 |

As can be seen from Table III, the latex which contained only 4 ppm of silver ions as a bactericide protected the latex until the fifth inoculation over a period of eight days. Thus, the low level of silver ions again proved to provide the latex with a degree of protection against bacterial growth. However, Examples 13, 15 and 16 showed that outstanding protection against bacterial growth is provided by utilizing a combination of silver ions and organic chemical bactericide. In fact, the degree of protection against bacterial growth exhibited in Example 13 is much better than the protection against bacterial growth exhibited in Example 10 where twice as much of the Biochek 430 bactericide was utilized. Example 15 shows that 750 ppm of Nalco VX5357 bactericide used in conjunction with only 2 ppm of silver ions provides the same level of inhibition to bacterial growth as does the use of twice as much Nalco VX5357 bactericide without silver ions. Examples 12 and 16 show that the amount of Promexal X50 bactericide can be cut in half if used in conjunction with only 2 ppm of silver ions without a significant loss in protection against bacterial growth.

EXAMPLES 17–21

The procedure described in Examples 5–9 was repeated in this series of experiments except for the fact that latex samples which had been shelf-aged for two months were used rather than fresh latex samples. The results of this testing are reported in Table IV.

TABLE IV

| Ex. | Bactericide | Inoculations | Days |
|---|---|---|---|
| 17 | Biochek 430 - 1500 ppm | 10 | 13 |
| 18 | Nalco VX5357 - 1500 ppm | 10+ | 13+ |
| 19 | Promexal X50 - 1000 ppm | 9 | 12 |
| 20 | Biochex 430 - 750 ppm Silver ions - 4 ppm | 9 | 12 |
| 21 | Silver ions - 4 ppm | 1 | 1 |

Example 20 again shows that outstanding protection against bacterial growth is provided by utilizing a combination of silver ions and an organic chemical bactericide. In fact, the degree of protection against bacterial growth exhibited in Example 20 is essentially the same as the protection against bacterial growth exhibited in Example 17 where twice as much of the Biochek 430 bactericide was utilized. Example 21 does not show good protection against bacteria growth which may be attributable to the level of silver ions diminishing over time because of precipitation of the silver nitrate which was utilized as the source of silver ions.

EXAMPLES 22–26

The procedure described in Examples 5–9 was repeated in this series of experiments except for the fact that latex samples were inoculated with 0.1 cc portions of the contaminated latex sample rather than 1.0 cc portions of the contaminated latex samples. The results of this testing are reported in Table V.

TABLE V

| Ex. | Bactericide | Inoculations | Days |
|---|---|---|---|
| 22 | Biochek 430 - 1500 ppm | 19 | 30 |
| 23 | Nalco VX5357 - 1500 ppm | 24+ | 35+ |
| 24 | Promexal X50 - 1000 ppm | 24 | 35+ |
| 25 | Biochex 430 - 750 ppm Silver ions - 4 ppm | 10 | 17 |
| 26 | Silver ions - 4 ppm | 6 | 11 |

This series of experiments shows the same general trends as was experienced in Examples 5–9.

EXAMPLES 27–31

The procedure described in Examples 5–9 was repeated in this series of experiments except for the fact that latex samples were inoculated with 0.1 cc portions of the contaminated latex sample rather than 1.0 cc portions of the contaminated latex samples and except for the fact that latex samples which had been shelf-aged for one month were used rather than fresh latex samples. The results of this testing are reported in Table VI.

TABLE VI

| Ex. | Bactericide | Inoculations | Days |
|-----|-------------|--------------|------|
| 27 | Biochek 430 - 1500 ppm | 3 | 4 |
| 28 | Nalco VX5357 - 1500 ppm | 22+ | 37+ |
| 29 | Promexal X50 - 1000 ppm | 22+ | 37+ |
| 30 | Biochex 430 - 750 ppm Silver ions - 4 ppm | 14 | 26 |
| 31 | Silver ions - 4 ppm | 7 | 13 |

This series of experiments shows the same general tread as were shown in Examples 5–9. As can be seen from Example 31, the latex which contained only 4 ppm of silver ions as a bactericide protected the latex until the seventh inoculation over a period of 13 days. Thus, the silver ions alone provided the latex with protection against bacterial growth. However, Example 30 again shows that outstanding protection against bacterial growth is provided by utilizing a combination of silver ions and organic chemical bactericide. In fact, the degree of protection against bacterial growth exhibited in Example 30 is better than the protection against bacterial growth exhibited in Example 27 where twice as much of the Biochek 430 bactericide was utilized.

While certain representative embodiments and details have been shown for the purpose of illustrating the subject invention, it will be apparent to those skilled in this art that various changes and modifications can be made therein without departing from the scope of the subject invention.

What is claimed is:

1. A method of inhibiting the growth of bacteria in latex which comprises incorporating into the latex so as to contact said bacteria, at least a bactericidally effective amount of ions of a metal from Group Ib of the Periodic Chart and an organic chemical bactericide.

2. A latex which is comprised of (1) a polymer, (2) water, (3) an emulsifier, (4) ions of a metal from Group Ib of the Periodic Chart, and an organic chemical bactericide.

3. A method as specified in claim 1 wherein the ions of the metal from Group Ib are silver ions.

4. A latex as specified in claim 2 wherein the ions of a metal from Group Ib of the Periodic Chart are silver ions.

5. A latex as specified in claim 4 wherein the silver ions are present at a concentration which is within the range of about 1 ppm to about 50 ppm.

6. A latex as specified in claim 4 wherein the silver ions are present at a concentration which is within the range of about 2 ppm to about 10 ppm.

7. A latex as specified in claim 6 wherein the organic chemical bactericide is present in an amount which is within the range of about 300 ppm to about 1000 ppm.

8. A latex as specified in claim 7 wherein the organic chemical bactericide is selected from the group consisting of 2-methyl-4,5-trimethylene-4-isothiazolin-3-one, 1,2-dibromo-2,4-dicyanobutane, 2-bromo-2-nitro-1,3-propanediol, methylene bis(thiocyanate), 1,2-dibromo-2,4-dicyano-butane, and 2-bromo-2-nitro-1,3-propanediol.

9. A latex as specified in claim 7 wherein from about 0.005 phm to about 0.5 phm of said emulsifier is present.

10. A latex as specified in claim 9 wherein said polymer is a rubbery polymer.

11. A latex as specified in claim 10 wherein said rubbery polymer is selected from the group consisting of styrene-butadiene rubber, carboxylated styrene-butadiene rubber, polybutadiene rubber, nitrile rubber and carboxylated nitrile rubber.

12. A latex as specified in claim 11 wherein said latex has a solids content which is within the range of about 1 weight percent to about 70 weight percent.

13. A latex as specified in claim 11 wherein said latex has a solids content which is within the range of about 30 weight percent to about 60 weight percent.

14. A latex as specified in claim 13 wherein said silver ions are present at a concentration which is within the range of about 3 ppm to about 5 ppm.

15. A method as specified in claim 3 wherein said silver ions are present at a concentration which is within the range of about 1 ppm to about 50 ppm.

16. A method as specified in claim 15 wherein the silver ions are incorporated into the latex by the addition of at least one member selected from the group consisting of silver acetate, silver bromide, silver carbonate, silver chlorate, silver chloride, silver citrate, silver fluoride, silver iodate, silver lactate, silver nitrate, silver nitrite, silver perchlorate and silver sulfide.

17. A method as specified in claim 15 wherein the silver ions are incorporated into the latex by the addition of silver nitrate.

18. A method as specified in claim 15 wherein the silver ions are incorporated into the latex by an electrolytic process.

19. A method as specified in claim 1 wherein the ions of a metal from Group Ib of the Periodic Chart are silver ions; wherein said silver ions are present at a concentration which is within the range of about 2 ppm to about 4 ppm; and wherein the said organic chemical bactericide is present at a concentration which is within the range of about 300 ppm to about 1000 ppm.

20. A latex as specified in claim 2 wherein the ions of a metal from Group Ib of the Periodic Chart are silver ions; wherein said silver ions are present at a concentration which is within the range of about 2 ppm to about 4 ppm; and wherein the said organic chemical bactericide is present at a concentration which is within the range of about 300 ppm to about 1000 ppm.

* * * * *